United States Patent
Markman et al.

(10) Patent No.: US 7,718,813 B2
(45) Date of Patent: May 18, 2010

(54) HYDROLYSIS AND PURIFICATION OF ACTIVE PLANT COMPOUNDS SUITABLE FOR TOPICAL APPLICATION

(75) Inventors: Leonid Markman, Fair Lawn, NJ (US); Mark Shlyankevich, Waterbury, CT (US)

(73) Assignee: Nature Pure Labs SW, Inc., Brooklyn, NY (US)

( * ) Notice: Subject to any disclaimer, the term of this patent is extended or adjusted under 35 U.S.C. 154(b) by 1878 days.

(21) Appl. No.: 10/641,945

(22) Filed: Aug. 15, 2003

(65) Prior Publication Data

US 2005/0037099 A1 Feb. 17, 2005

(51) Int. Cl.
*C07D 311/36* (2006.01)
(52) U.S. Cl. ....................................................... 549/403
(58) Field of Classification Search ................. 549/403; 514/456
See application file for complete search history.

(56) References Cited

U.S. PATENT DOCUMENTS

| | | | |
|---|---|---|---|
| 5,679,806 A * | 10/1997 | Zheng et al. | 549/403 |
| 5,824,702 A | 10/1998 | Wei et al. | |
| 5,871,743 A * | 2/1999 | Chajuss | 424/757 |
| 6,030,620 A | 2/2000 | Pillai et al. | |
| 6,060,070 A * | 5/2000 | Gorbach | 424/401 |
| 6,261,565 B1 | 7/2001 | Empie et al. | |
| 6,280,777 B1 | 8/2001 | Bombardelli et al. | |
| 6,352,685 B2 | 3/2002 | Hoshino et al. | |
| 6,455,032 B1 | 9/2002 | Kelly et al. | |
| 6,482,448 B2 | 11/2002 | Tabor | |
| 6,680,381 B1 * | 1/2004 | Waggle et al. | 536/8 |

OTHER PUBLICATIONS

Punnonen, et al., *Ann. Chirurg. Gynecol.*, Abstract only, 76(suppl. 202):39-41 (1987).
Schmidt, et al., *Maturitas, Journal of the Climacteric & Postmenopause*, 20:25-30 (1994).
Schmidt, et al., *Int. J. Dermatol.*, 35(9):669-674 (1996).
Reinli, et al., *Nutr. Cancer*, 26:123-148 (1996).
Miksicek, R.J., *Proc. Soc. Exp. Biol. Med.*, 208:44-50 (1995).
Cassidy, A., *Intl. J. Vitamin & Nutr. Res.*, Abstract only, 73(2):120-126 (2003).
Kang, et al., *J. Invest. Dermatol.*, 120(5):835-841 (2003).
Wollenweber, et al.; *Planta Medica*, Abstract only, 69(1):15-20 (2003).
Watanabe, et al., *Jap. J. Cancer Chemother.*, Abstract only, 30(7):902-908 (2003).
Walter, E.D., *J. Amer. Chem. Soc.*, 63:3273-3276 (1941).
Beauregard, et al., *Arch. Dermatol.*, 123:1638-1643 (1987).
Chung, et al., *J. Dermatol. Sci.*, Abstract only, 15(3):188-200 (1997).
Vázquez, et al., *Maturitas, Journal of the climacteric & Postmenopause*, 25:209-215 (1996).
Strauss, et al., *J. Invest. Dermat.*, 39:139-155 (1962).
Brincat, et al., *Br. J. Obstet. Gynecol.*, 94:126-129 (1987).
Brincat, et al., *Br. J. Obstet. Gynecol.*, 92:256-259 (1985).
Dunn, et al., *Arch. Dermatol.*, 133:339-342 (1997).
Adlercreutz, et al., *Lancet*, 339:1233 (1992).
Kaziro, et al., *J. Endocr.*, 103:395-399 (1984).
Choi, S., *Arch. Pharm. Res.*, Abstract only, 25(1):71-76 (2002).
Li, et al., *Acta Pharmacologica Sinica*, Abstract only, 20(6):551-554 (1999).
Morreale, et al., *Biochem. Mol. Biol. Int.*, Abstract only, 42(6):1093-1102 (1997).
Aviram, et al., *Ann. Nutr. Metab.*, 37:75-83 (1993).
Wei, et al., *Proc. Soc. Exp. Biol. Med.*, Abstract only, 208:124-130 (1995).
Wei, et al., *Nutr. Cancer*, 20(1):1-12 (1993).
Maheux, et al., *Am. J. Obstet. Gynecol.*, 170:642-649 (1994).
Uckun, et al., *Science*, 267:886-891 (1995).

* cited by examiner

*Primary Examiner*—Johann R Richter
*Assistant Examiner*—Ali Soroush
(74) *Attorney, Agent, or Firm*—Modern Times Legal; Robert J. Sayre

(57) ABSTRACT

A composition suitable is disclosed for topical application for preventing and treating changes associated with skin aging and formation of abnormal skin lesions. The composition is derived by hydrolyzing a source composition in an acidic solution. The source composition can be, e.g., a soy composition and can include one or more isoflavones, phytoestrogens, sitosterols and saponins. After hydrolysis, water is added to the acidic solution to produce a first precipitate, which is then dissolved in an alcohol solution. The alcohol solution is then separated from undissolved portions of the first precipitate, and the alcohol in the separated alcohol solution is eliminated to produce a second precipitate of solids that were dissolved in the alcohol. This second precipitate is then dissolved in an organic solvent to produce a composition suitable for inclusion in a dermatological or cosmetic preparation.

11 Claims, No Drawings

HYDROLYSIS AND PURIFICATION OF ACTIVE PLANT COMPOUNDS SUITABLE FOR TOPICAL APPLICATION

BACKGROUND

Topical application of estrogenic hormones (e.g., estradiol and estriol compounds) have been shown to markedly improve the elasticity and firmness of skin and to decrease the wrinkle depth and pore sizes. Phytoestrogens are naturally occurring plant compounds that behave similarly to estrogen in the body.

Isoflavones are known phytoestrogens; and they are found, for example, in soy products and are known to have systemic effects in the prevention of cardiovascular diseases, osteoporosis, malignant tumors and other maladies in humans. The current literature supports the safety of isoflavones as typically consumed in diets based on soy or containing soy products.

A number of proposed techniques have been directed to the oral ingestion of the isoflavone compositions. Though, other methods have been proposed for topical application of an isoflavone for blocking ultraviolet radiation to lessen or prevent skin sunburns, premature aging and skin cancer.

Although there are some industrial and laboratory methods for isoflavone purification, the high cost of these compounds limits creation of widely available cosmetic or dermatological preparations.

SUMMARY

Described herein is a simple and inexpensive semi-industrial technology for isolation and purification of active plant compounds, including isoflavones, sitosterols, saponins (sapogenins), and phospholipids. Soybeans are particularly suitable as a plant source; however, any other isoflavone-containing plants (e.g., red clover and kudzu) can be uses as a source of active compounds. Molasses, enriched fluor or any other non-protein concentrate can be used as a source material for the isolation and purification process.

The isolation and purification process commences with the hydrolysis of a source composition (e.g., a soy concentrate including isoflavones) in an acidic solution. Water is then added to the acidic solution to produce a first precipitate, which is then dissolved in an alcohol solution. The alcohol solution is separated from undissolved portions of the first precipitate, and the alcohol in the separated alcohol solution is removed (e.g., via evaporation or via a settling process) to produce a second precipitate of solids that were dissolved in the alcohol. This second precipitate is then dissolved in an organic solvent to produce a product having a heightened isoflavone concentration.

The product of the isolation and purification process can be introduced into cosmetic compositions or dermatological preparations that are then topically applied, e.g., for the prevention and treatment of skin aging, treatment of increasing skin thickness, acne treatment, cellulite treatment, sensitive skin treatment, wound healing, arthritis treatment, hair loss treatment, and in the form of patches for prostate treatment. Because isoflavones have no known side effects as a hormone replacement therapy substitute, isoflavones can also be used for treatment of some dermatological diseases such as psoriasis and eczema by means of topical application to the skin.

In the preparation of a topical composition, plant compounds that manifest weak estrogenic activity (i.e., phytoestrogens) are substituted for natural or synthetic estrogens. The phytoestrogens (e.g., isoflavones) do not provoke the harmful systemic or side effects that are provoked by estrogen treatments. The weak estrogenic properties of naturally occurring isoflavones, their derivatives and related compounds allow for their utilization in replacing weakened estrogen stimulation of aged skin. Other active soybean compounds offer additional benefits to the skin.

DETAILED DESCRIPTION

Skin senescence is an inevitable process. There are many dermatologic signs and symptoms that have been associated with menopause. Age-dependent involutional changes in women are manifested in skin as wrinkles, dryness and laxity, and a set of other cutaneous symptoms such as seborrheic keratoses and dermatitis, lentigines, ecchymoses, hirsutism or hair loss, varicosities, etc. The most-common dermatologic diagnoses in an elderly population (95-85%) were elastosis (degenerative changes in elastic tissue), onychorrhesis (abnormal brittleness of nails), and xerosis (evolutionary sclerosis of tissues), which result from age-related changes in production and maturation of extracellular fibers, collagen and elastin. These degenerative processes are produced by general involution, in which the hormonal status seems to be the most significant factor.

Topical application of estradial increases the number and thickness of elastic fibers in menopausal patients. Studies have shown that estrogen prevents skin aging, preserves skin collagen content, elastic properties and thickness. In postmenopausal women, the systemic (oral) estrogen substitution has been associated with substantial and statistically significant reduction (25 and 30% lower) of senile dry skin and skin wrinkling.

However, both oral and local (topical) estrogen therapy has significant limitations, and the hormone concentration and size of application should be restricted to reduce the risk of systemic side effects. Some women are sensitive to estrogen application and may suffer from estrogen dermatitis as a result. Moreover, chronic estrogen exposure can stimulate age-related disorders and precancerous lesion formation.

Benefits that are the same or similar to those provided by estrogen compounds can be provided by phytoestrogens, which manifest weak estrogenic activity without provoking the harmful systemic or side effects.

Soybean phytoestrogens include the isoflavones, daidzein and genistein, as well as several minor compounds (e.g., glycitin, and acetyl forms) and non-isoflavone phytoestrogen coumestrol. In raw soybeans and nonfermented soy products (soy flour, powder, tofu, soy nuts, etc.), these isoflavones are conjugated with glucose (glycosides), and are named, daidzin and genistin. After fermentation by bacteria or chemical hydrolysis, these glycosides lose sugar and convert into free forms (aglucones). For topical application, the unconjugated (free) isoflavones only are used.

Besides isoflavones and coumestrol, soy includes other active nonprotein substances, such as the following:
  Phospholipids: phosphatidyl ethanolamine (cephalin), phosphatidyl choline (lecithin);
  Phytosterols: sitosteryl-D-glucoside (beta-sitosterol); and
  Saponins: soyasapogenols A, B, C, D, E, or their aglucons-sapogenins.

Evidence of the functional activities of these soybean compounds is described, as follows:

Phytoestrogens:

Phytoestrogens, which are the plant compounds that are structurally and functionally related to the sex hormone estrogen, may including the following group of isoflavones:

genistein, daidzein, glycitein, biochanin, santal, orobol, pratensein, equol and prunetin. All naturally occurring isoflavones and their derivatives exhibit several key functions such as partial estrogen receptor binding, antioxidant activity, stimulation of cell differentiation, anticancer effect, anti-inflammatory properties, and DNA repair. These functions make this class of molecules desirable as topical agents in the treatment of numerous skin disorders and multiple systemic disorders.

Phytoestrogens and their metabolites interact with specific estrogen cell receptors, and compete with endogenous hormone molecules, but they can provoke a weak estrogenic response. This dual "weak" action leads to normalization of estrogen effect both at the elevated or decreased levels of endogenous hormone.

Phytosterols:

Phytosterols are structurally similar to the animal cholesterol. Plant sterols found in the skin surface lipids of humans originate from diet and are absorbed in the intestine into plasma and then transferred to the skin.

Saponins:

Saponins can promote wound healing and can stimulate epidermal cell proliferation and epidermis formation in a dose-dependent manner. Saponins can also enhance the expressions of protein factors related to cell proliferation, namely, epidermal growth factor and its receptor, fibronectin and its receptor, keratin, and collagenase I. Further, saponins can improve blood flow in peripheral tissues, inhibit itch, improve atopic dermatitis, and reduce inflammation.

Phospholipids:

Compositions including phospholipids have been developed for local treatment of venous and microcirculatory alterations (e.g., varicose veins, chronic venous insufficiency, associated signs and symptoms) and sport injuries (e.g., bruises, swelling secondary to sprains and contusions).

The benefits that can be derived from topical application of these compositions are believed to be superior to those that can be derived via systemic ingestion for the following reasons. The bioavailability of isoflavones through the skin is believed to be greater than the bioavailability of isoflavones through gastrointestinal absorption because topical application does not afford an opportunity for the isoflavones to be converted into inactive compounds in the gut before reaching the skin. Additionally, the local concentration of isoflavones may be higher in a topical composition, where the isoflavone concentration can reach the high levels needed for some effects that are doubtful under oral administration (e.g., antioxidant and anti-promotional activity, cell differentiation, etc.). Moreover, treatment can be localized via topical application, as some dermatological diseases, such as psoriasis and eczema, usually have a local orientation; and localized topical application of the active, naturally occurring blend of isoflavones, phospholipids, sitosterols and saponins can be helpful for delay of these processes in the areas of greatest suffering (e.g., facial and hand skin).

Additionally, the isoflavones can be used independently or introduced into known topical compositions as an additional compound with an adjuvant purpose. Further still, the absence of any known side effects as a result of topical isoflavone treatment, enables its application to skin for the prevention of skin aging and increasing skin thickness, acne treatment, anti-cellulite treatment, sensitive skin treatment, wound healing, arthritis treatment, hair loss treatment, in prostate treatment patches, and for treatment of other dermatological problems and diseases.

The topical cosmetic or dermatological composition can be applied to skin to treat or prevent the following changes associated with aging of the skin.

Formation of Rhytides:

The formation of rhytides, or wrinkles, of the skin likely results from a loss of normal elastin fibers and alteration of collagen in the dermis, which occurs with aging and is accelerated by chronic exposure to the sun. These changes have been postulated to result from free-radical damage to these fibers directly and to the fibroblast cells that produce them.

Xerosis:

Xerosis, or dryness associated with aging, results from a decrease in the epidermal water barrier function, which is related to a decrease in differentiation of aging epidermal keratinocytes.

Telangiectasis:

Telangiectasis, so-called "broken blood vessels," are capillary loop proliferations related to chronic sun exposure as well as to chronic estrogen exposure.

Dispigmentation:

Dispigmentation changes seen with aging include hyperpigmented ephilides (freckling), lentigines ("sun spots"), and melasma. The latter is known to be worse in the setting of chronic estrogen exposure.

The topical cosmetic or dermatological composition can also be applied to skin to treat or prevent changes associated with formation of precancerous lesions.

Process for Hydrolysing and Purifying Isoflavones, Phospholipids, Sitosterols and Saponins:

The following description covers a laboratory process for hydrolyzing and purifying isoflavones; the process can readily be scaled up for larger-scale purification.

In a first stage, one part of concentrated powder including about 40% of isoflavones by weight in glucoside form is dissolved in 5-23 parts (weight/volume) of alcohol (e.g., methanol) and stirred. Concentrated powders with the relatively high isoflavone content are available as, e.g., SOY ISOFLAVONES 40% (food grade) from DNP International Co., Inc. (Whittier, Calif., USA); or KUDZU EXTRACT (Pueraria Lobata) 40% isoflavones content from International Additive Concepts (Charlotte, N.C., USA). 0.5-8.0 parts (weight/volume) of concentrated acid (e.g., hydrochloric) is added to the solution. The mixture is heated to 50-75° C., where it is maintained for 4-7 hours, and then cooled.

In a second stage, cool distilled water is added at twice the volume of the above-described mixture and the resulting solution is mixed intensively. Isoflavones and other substances form a coarse, dark-brown precipitate, which is separated and collected.

In a third stage, the dark-brown precipitate from the second stage is dissolved in 10-25 parts (weight/volume) of 60% ethanol (40% water) on a stirrer for several hours at room temperature. Alternatively, other alcohols can be used. The solution is left to stand at room temperature overnight, and a gray pellet of insoluble substances remains in the solution. The supernatant is removed, and the pellet is placed in 5 parts (weight/volume) of fresh 60% ethanol to provide additional extraction, though a small white precipitate remains. The supernatant is again removed and combined with the first supernatant. The ethanol and water in the combined supernatant are evaporated, and dark-red or pale-yellow crystals appear.

In a fourth stage, these crystals are dissolved in organic solvent (e.g., a glycol composition, such as glycerin, propylene glycol, butylene glycol, pentylene glycol, polyethylene glycol, etc.). This new composition can then be incorporated into a topical cosmetic or dermatological composition.

Examples of beauty products and cosmetics in which the composition can be incorporated include after-shave lotions, after-sun lotions, anti-aging cream, baby lotion, bath oil, body cream, body emulsions, body mask creams, body mask lotions, body masks, body oil, cosmetic pads, eye cream, hand cream, night cream, eye gels, facial creams, facial emulsions, facial masks, hair gels, hair care preparations, hair lotions, hair pomades, lipsticks, skin moisturizers, sun tan lotion, fragrances, soaps, essential oil for personal care, hair and scalp treatment ampoules, facial ampoules, hair serums, facial serums, skin clarifiers, skin emollients, skin lighteners, lotions and other products (e.g., creams, serums, etc.) for cellulite reduction, skin toners, lip balm, hair mask, hair cream, patches, and aromatherapy preparations.

In describing embodiments of the invention, specific terminology is used for the sake of clarity, though the scope of the actual invention may not be so limited. In addition, it should be understood that in some instances where a particular embodiment of the invention includes a plurality of components or method steps, those components or steps may be replaced with a single component or step. Likewise a single component or step may be replaced by a plurality of components or steps.

While this invention has been shown and described with references to particular embodiments thereof, those skilled in the art will understand that various changes in form and details may be made therein without departing from the scope of the invention, which is limited only by the following claims.

What is claimed is:

1. A method for producing a composition for topical application, the method comprising:
   a) hydrolyzing a source composition including an isoflavone in an acidic solution, wherein the isoflavone loses a sugar component and is converted into an aglycone during hydrolysis;
   b) adding water to the acidic solution to produce a first precipitate that includes the aglycone;
   c) dissolving the first precipitate in an alcohol solution, wherein the aglycone joins the alcohol solution;
   d) separating the alcohol solution including the aglycone from undissolved portions of the first precipitate;
   e) removing the alcohol from the separated alcohol solution to produce a second precipitate of solids that were dissolved in the alcohol, wherein the second precipitate includes the aglycone; and
   f) dissolving the second precipitate including the aglycone in an organic solvent to produce a composition suitable for inclusion in a dermatological or cosmetic preparation.

2. The method of claim 1, wherein the source composition includes a composition from a plant.

3. The method of claim 2, wherein the plant is selected from the group consisting of soy, clover, kudzu and combinations thereof.

4. The method of claim 3, wherein the source composition includes an enriched soy composition.

5. The method of claim 4, wherein the enriched soy composition also includes one or more sitosterols, saponins, coumesterol, and phospholipids.

6. The method of claim 1, wherein the source composition comprises the isoflavones daidzein and genistein.

7. The method of claim 1, wherein the acidic solution comprises alcohol and an inorganic acid.

8. The method of claim 7, wherein the inorganic acid comprises hydrochloric acid.

9. The method of claim 1, wherein the organic solvent is a glycol composition.

10. The method of claim 1, further comprising applying the topical composition to skin of a living organism.

11. The method of claim 10, wherein the topical composition is applied to skin at or adjacent to a locale subject to a condition selected from the group consisting rhytides of the skin, xerosis, telangiectasis, skin dispigmentation, increased skin thickness, acne, cellulite, skin sensitivity, a wound, arthritis, hair loss, prostrate disease, menopausal or postmenopausal symptoms, psoriasis and eczema.

* * * * *